Figure 3:
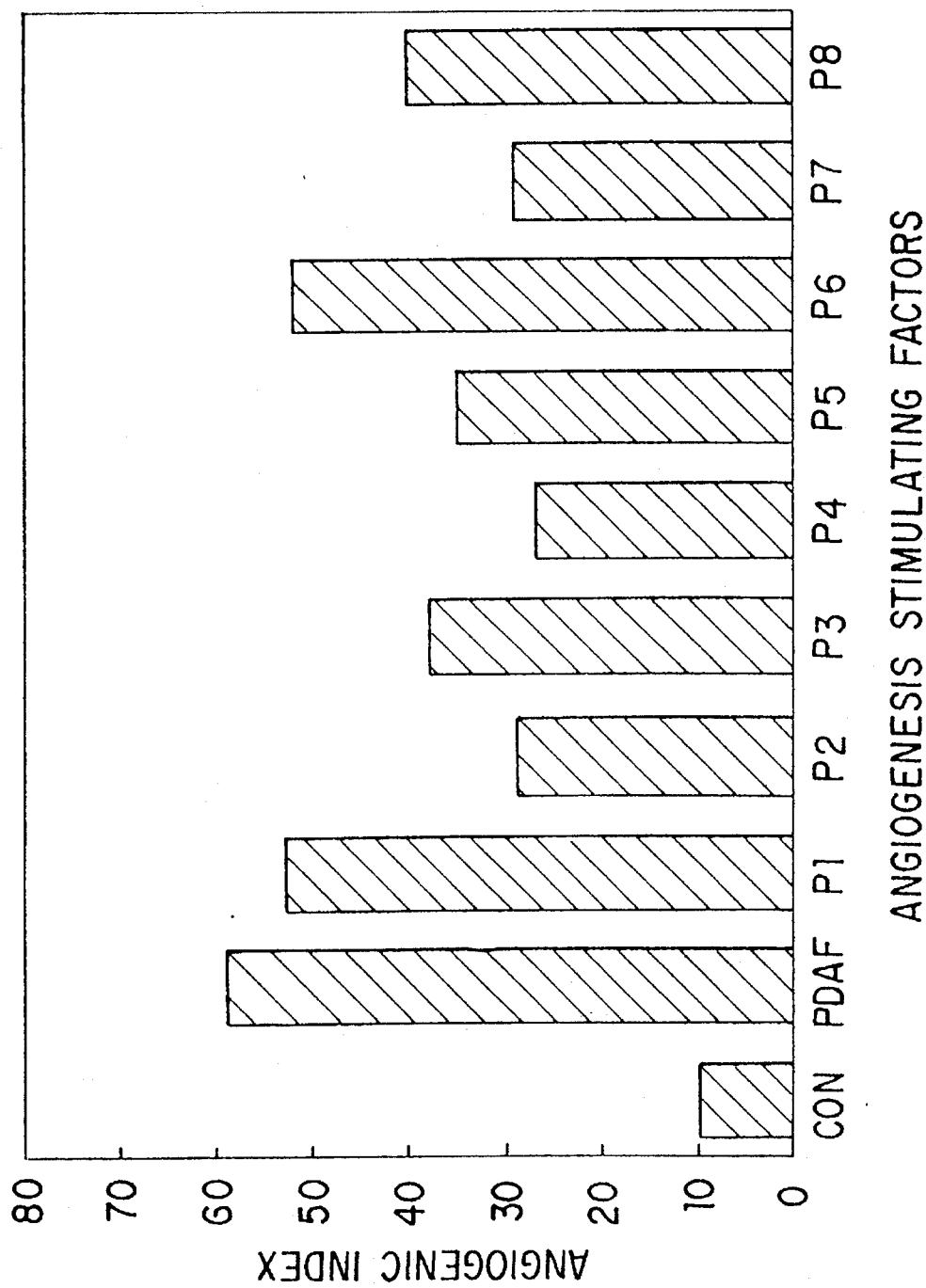

United States Patent [19]

Whitman et al.

[11] Patent Number: 5,470,831
[45] Date of Patent: Nov. 28, 1995

[54] ANGIOGENIC PEPTIDES

[75] Inventors: Russell B. Whitman, Dix Hills; Robert Wohl, South Setauket; Ronald G. Duff, East Moriches, all of N.Y.

[73] Assignee: Curative Technologies, Inc., Setauket, N.Y.

[21] Appl. No.: 37,486

[22] Filed: Mar. 24, 1993

Related U.S. Application Data

[63] Continuation of Ser. No. 631,823, Dec. 21, 1990, abandoned.
[51] Int. Cl.$^6$ .................... C07K 5/10; C07K 7/06; A61K 38/07; A61K 38/08
[52] U.S. Cl. .................... 514/16; 514/15; 514/17; 514/18; 530/330; 530/329; 530/328
[58] Field of Search .................... 514/13, 18, 17, 514/16, 15; 530/330, 331, 329, 328

[56] References Cited

U.S. PATENT DOCUMENTS 4,645,828  2/1987  Twardzik et al. .................... 530/324

FOREIGN PATENT DOCUMENTS 0378364  1/1989  European Pat. Off. .

OTHER PUBLICATIONS

Cortellaro et al., 1990, Thrombosis Res. 58:571–576.
Eisman et al., 1990, Blood, vol. 76, No. 2 (Jul. 15), pp. 336–344.
Medici et al., 1989, Thrombosis Res. 54:277–287.
Rybak et al., 1989, Blood, vol. 73, No. 6 (May 1), pp. 1534–1539.
Zucker et al., 1989, Proc. Natl. Acad. Sci. USA 86:7571–7574.
Bebawy et al., 1986, J. Leukocyte Biol. 39:423–434.
Guastamacchia et al., 1985, Boll. Soc. It. Biol., No. 4, vol. LXI, pp. 499–505.
Schmitz–Huebner et al., 1984, Thrombosis Res. 34:277–285.
Weerasinghe et al., 1984, Thrombosis Res. 33:625–631.
Banda et al., 1982, Proc. Natl. Acad. Sci. USA 79:7773–7777.
Bernstein et al., 1982, J. Cell. Sci. 56:71–82.
Gimbrone, Jr., et al., 1974, J. Natl. Cancer Institute, vol. 52, No. 2, pp. 413–427.
Aoyagi et al., 1988, "Interaction of basic extension peptide fragments of adrenodixon precursor with phospholipid vesicles", Int. J. Peptide Protein Res. 32:406–414.
V. LaRussa et al.; "Effects of Anti–CD33 Blocked Ricin Immunotoxin on the Capacity of CD34 Human Marrow Cells to Establish in vitro Hematopoiesis in Long–term Marrow Cultures" *Exp. Hematol.*, 20:442–448 (1992).
A. Engert et al.; "Resistance of Myeloid Leukaemia CE11 Lines to Ricin A–Chain Immunotoxins" *Leukemia Research* 15:1079–1086, No. 15 (1991).
J. Lambert et al.; "An Immunotoxin Prepared with Blocked Ricin: A Natural Plant Toxin Adapted for Therapeutic Use" *Cancer Research*, 51:6236–6242 (1991).
D. Roy et al.; "Anti–MY9–Block–Ricin: An Immunotoxin for Selective Targeting of Acute Myeloid Leukemia Cells" *Blood*, 77:2404–2412 (1991).
Ciaglowski et al. Arch. Biochem. Biophys. vol. 250 No. 1 (1986) 249–256.

*Primary Examiner*—Jill Warden
*Assistant Examiner*—Carol A. Salata
*Attorney, Agent, or Firm*—Pennie & Edmonds

[57] ABSTRACT

The present invention relates to peptides and peptide derivatives related to platelet factor 4 which exhibit angiogenic activity, to pharmaceutical compositions comprising said peptides, and to methods for promoting angiogenesis utilizing said peptides. It is based, in part, on the discovery that an octapeptide derived from platelet factor 4 and seven structurally related peptides (depicted in FIG. 1) are capable of inducing an angiogenic response in vivo as measured by neovascularization in rabbit corneal implant assay and by measurement of capillary endothelial cell chemoattraction. The angiogenic peptides of the invention may be particularly useful in promoting wound healing, including incisional healing, bone repair, burn healing, and post-infarction repair in myocardial injury, and in facilitating the assimilation of grafted tissues, particularly in persons suffering from vascular insufficiency, such as diabetic patients.

16 Claims, 4 Drawing Sheets

| | | | | | | | | | | | |
|---|---|---|---|---|---|---|---|---|---|---|---|
| 1 | | Thr | Thr | Ser | Gln | Val | Arg | Pro | Arg | | |
| 2 | Val | Lys | Thr | Ser | Gln | Val | Arg | Pro | Arg | | |
| 3 | | | Thr | Ser | Gln | Val | Arg | Pro | Arg | | |
| 4 | | | | | Ser | Val | Arg | Pro | Arg | | |
| 5 | | Thr | Thr | Ser | Gln | Val | Arg | Pro | Arg | His | Ile | Thr |
| 6 | | Thr | Thr | Ser | Gln | Val | | | | | |
| 7 | | | Thr | Ser | Gln | Val | Arg | | | | |
| 8 | | Thr | Thr | Ser | Gly | Ile | His | Pro | Lys | | |

FIG. 1

E A E E D G D L Q C L C V K T T S Q V R P R H I T S L E V
I K A G P H C P T A Q L I A T L K N G R K I C L D L Q A P L
Y K K I I K K L L E S

| THREE-LETTER ABBREVIATION | ONE-LETTER SYMBOL |
|---|---|
| Ala | A |
| Arg | R |
| Asn | N |
| Asp | D |
| Asx | B |
| Cys | C |
| Gln | Q |
| Glu | E |
| Glx | Z |
| Gly | G |
| His | H |
| Ile | I |
| Leu | L |
| Lys | K |
| Met | M |
| Phe | F |
| Pro | P |
| Ser | S |
| Thr | T |
| Trp | W |
| Tyr | Y |
| Val | V |

FIG. 2

ANGIOGENIC PEPTIDES

This application is a continuation of U.S. patent application Ser. No. 07/631,823 filed Dec. 21, 1990 now abandoned.

1. INTRODUCTION

The present invention relates to peptides and peptide derivatives related to platelet factor 4 which exhibit angiogenic activity, to pharmaceutical compositions comprising said peptides, and to methods of promoting angiogenesis utilizing the peptides of the invention.

2. BACKGROUND OF THE INVENTION

The biological process of neovascularization (otherwise known as angiogenesis, the formation of new blood vessels) is necessary for normal development and is also an important aspect of wound repair, pathological conditions like inflammation, and solid tumor growth (Leibovich et al., 1988, in "Growth Factors and Other Aspects of Wound Healing," Barbul et al., eds., Alan R. Liss, N.Y. p. 132). The angiogenic cascade involves endothelial cell migration, protease production and endothelial cell proliferation (Leibovich et al., supra). Many well known and variously characterized autocrine and paracrine growth factors are involved in the angiogenic cascade. One of the lesser characterized factors is Platelet Derived Angiogenesis Factor (PDAF; Banda et al., 1982, Proc. Natl. Acad. Sci. 79:7773–7777).

2.1. Angiogenic Peptides

Several protein growth factors have been identified which induce angiogenesis. One of the best characterized angiogenic factors is basic fibroblast growth factor, a heparin-binding polypeptide mitogen. Basic fibroblast growth factor (bFGF) proteins have a molecular weight of about 18 kDa, consistent with the predicted cDNA translation product of 155 amino acids, although higher molecular weight forms have also been identified (Sommer et al., 1989, Biochem. Biophys. Res. Commun. 160:1267–1274; Abraham et al., 1986, EMBO J. 5:2523–2528).

A number of other factors have been reported to exhibit angiogenic activity, including ceruloplasmin (Chu and Olden, 1985, Biochem. Biophys. Res. Commun. 126:15–24); monocyte derived monocytoangiotropin (Wissler et al., 1983, Fed. Proc. 42, Abstract 684); placental angiogenic factor (Burgas, 1986, Eur. J. Clin. Invest. 16:486–493); glioma-derived endothelial cell growth factor (Libermann et al., 1987, EMBO J. 6:1627–1632); and a heparin-binding growth factor from adenocarcinoma of the kidney which is immunologically related to bFGF. A brief review of inflammation and angiogenesis may be found in Folkman et al, 1989, in "Progress in Immunology," Volume VII, Melchers, ed., Springer-Verlag, N.Y., pp. 761–764.

2.2. Platelet Factor 4

Platelet factor 4 (PF4), a 70 amino acid heparin-binding protein, is released from the alpha granules of activated platelets. The exact biological function of PF4 is not known, although PF4 is a member of a multigene family involved in chemotaxis, coagulation, inflammation, and cell growth (Eisman et al., 1990, Blood 76:336–344). The genomic sequence of the PF4 gene, and a highly homologous gene, PF4 alt, has recently been reported (Eismann et al., supra). Among the reported biological activities of PF4 are alleviation of concanavalin A-induced immunosuppression in mice (Zucker et al., 1989, Proc. Natl. Acad. Sci. 86:7571–7574); the ability to bind to and enter endothelial cells (Rybak et al., 1989, Blood 73:1534–1539); the elicitation of neutrophil chemotaxis, lysosomal enzyme release and increased adherence (Bebawy et al., 1986, J. Leukocyte Biol. 39:423–434); stimulation of migration of pericytes but not of smooth muscle cells nor endothelial cells (Bernstein et al., 1982, J. Cell. Sci. (56); 71–82); and a potential anti-thrombotic effect (Weerasinghe et al., 1984, Thromb. Res. 33:625–632). Increased levels of PF4 have been identified in diabetic patients (Guastamacchia et al., 1985, Boll. Soc. Ital. Biol. Sper. 61:499–502; Cortellaro et al., 1990, Thromb. Res. 58:571–576; Cella et al., 1986, Folia Haematol. 113:646–654) and in patients with Behcet's disease (Schmitz-Huebner and Knap, 1984, Thromb. Res. 34:277–286).

3. SUMMARY OF THE INVENTION

The present invention relates to peptides and peptide derivatives related to platelet factor 4 which exhibit angiogenic activity, to pharmaceutical compositions comprising said peptides, and to methods for promoting angiogenesis utilizing said peptides. It is based, in part, on the discovery that an octapeptide derived from platelet factor 4 and seven structurally related peptides (depicted in FIG. 1) were capable of inducing an angiogenic response in vivo as measured by neovascularization in rabbit corneal implant assay and by measurement of capillary endothelial cell chemoattraction. These eight peptides represent specific nonlimiting embodiments of the present invention.

The angiogenic peptides of the invention may be particularly useful in promoting wound healing, including incisional healing, bone repair, burn healing, and post-infarction repair in myocardial injury; and the assimilation of grafted tissues, particularly in persons suffering from vascular insufficiency, such as diabetic patients.

4. DESCRIPTION OF THE FIGURES

FIG. 1. Amino acid sequences of angiogenic peptides Wohl-1 through Wohl-8 (SEQ ID NO: 2–9).

FIG. 2. Amino acid sequence of PF4 (SEQ ID NO: 1).

FIG. 3. Bar graph showing angiogenic activities of Wohl 1–8 peptides (corresponding to P1–P8 corresponding to SEQ ID NOS: 2–9) compared to negative and positive (platelet derived angiogenic factor) controls.

Figure 4:
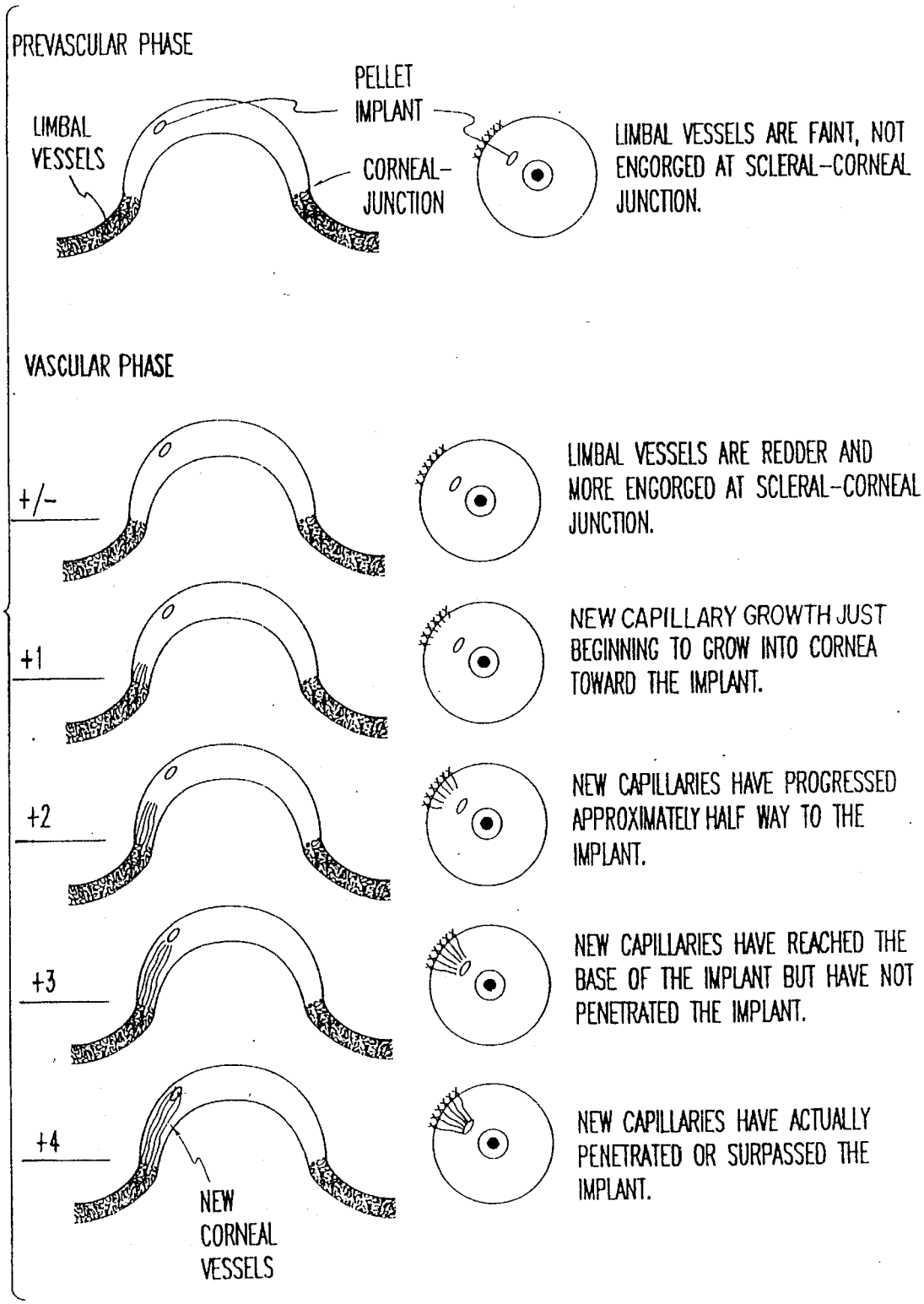

FIG. 4. Diagram for scoring capillary growth toward pellet implant.

5. DETAILED DESCRIPTION OF THE INVENTION

For purposes of clarity of disclosure, and not by way of limitation, the detailed description of the present invention is presented in the following subsections:

(i) preparation of platelet factor 4;

(ii) peptides of the invention and their preparation;

(iii) identification of angiogenic peptides; and (iv) utility of the invention.

5.1. Preparation of Platelet Factor 4

Platelet factor 4 (PF4) may be purified using any method known in the art. In a preferred embodiment of the invention, PF4 may be purified from thrombin-activated platelet extracts by a modification of the method described by Medici et al. (1989, Thrombos. Res. 54:277–287). The PF4 may be isolated by heparin sepharose affinity chromatography with elution of the factor at 1.7M NaCl, followed by strong anion exchange chromatography on a polysulfoethyl-aspartamide column eluted with NaCl in the presence of about 15% acetonitrile and finally by separation on a Vydac RPC₄ reverse phase HPLC analytical column eluted with a linear acetonitrile gradient in about 0.1% trifluoroacetic acid (TFA) in water.

5.2. Peptides of the Invention and Their Preparation

The peptides of the invention include any peptide which comprises either (i) at least a four amino acid portion of PF4, the amino acid sequence of which is set forth in FIG. 2 SEQ ID NO: 1, or a functionally equivalent sequence or (ii) at least a six amino acid sequence which is at least 66% homologous to a portion of PF4 sequence as set forth in FIG. 2 SEQ ID NO: 1, or a functionally equivalent sequence. Homology is to be construed herein as referring to identity between amino acid residues shared by different peptides; for example, a six amino acid residue peptide which is 66% homologous to a six amino acid fragment of PF4 shares 4 amino acid residues with the PF4 fragment which are not necessarily linked together.

In preferred embodiments of the invention, the peptide or peptide derivative comprises the sequence Thr-Ser-Gln (SEQ ID NO: 10) and/or Val-Arg-Pro (SEQ ID NO: 11), and more preferably Thr-Thr-Ser-Gln (SEQ ID NO: 12) and/or Val-Arg-Pro-Arg (SEQ ID NO: 5).

The peptides of the invention may also comprise portions which bear little or no homology to PF4. Furthermore, these peptides may be derivatized by conjugation to other compounds, including, but not limited to, carbohydrate, lipid, phosphate, starch, antibody, Fab, Fab₂, enzyme, amino acid, peptide, or growth factor compounds.

The amino acid sequence of PF4 as set forth in FIG. 2, or a functionally equivalent sequence, should be construed to mean that the PF4 sequence may be (i) that sequence set forth in FIG. 2 (SEQ ID NO: 1) or (ii) the sequence as set forth in FIG. 2 (SEQ ID NO: 1) but in which certain residues are substituted by functionally equivalent amino acids resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In all cases, the peptides of the invention exhibit angiogenic activity as defined in section 5.3, infra.

The peptides of the invention may be prepared by any method known in the art. For example, and not by way of limitation, the peptides may be synthesized (i) by cleavage from a larger peptide, such as, but not limited to, PF4; (ii) by recombinant DNA expression methods; and (iii) by chemical synthesis, including solid phase techniques as described by Barany and Merrifield (1980, in "The Peptides" Vol. 2, Gross and Meienhofer, eds., Academic Press, N.Y.).

In a preferred specific embodiment of the invention, tryptic digestion of PF4 may be performed to produce PF4 peptide fragments. For example, lyophilized PF4, prepared as described in section 5.1, may be dissolved in 50 µl of 0.4M $Na_2CO_3$/8M urea at pH=9 in a microcentrifuge tube. The protein may then be reduced by the addition of about 45 mM dithiothreitol in buffer at pH=8 for about 15 minutes at 50° C. The protein may then be carboxymethylated by addition of 5 µl of iodoacetic acid in 0.5N NaOH and incubated for about 15 minutes in the dark at room temperature. About 140 µl of deionized water and 5 µl of a 1 mM HCl solution of sequencer grade trypsin (at 200 µg/ml) may then be added and the sample incubated at 37° C. for about 24 hours. The resulting tryptic digest may then be injected into an appropriate reverse phase chromatography column, for example, a Vydac C18 column equilibrated with 2.7 percent acetonitrile/0.1 percent TFA/$H_2O$ and may be chromatographed at an appropriate flow rate, for example 0.5 ml/min with 1.0 minute fractions collected. The elution program may be, for example, 2.7 percent buffer B(95 percent acetonitrile) in buffer A (0.1 percent TFA in water) for about ten minutes, and a gradient of about 27–95 percent buffer B in 123 minutes. Elution of the peptides may be monitored spectrophotometrically at a wavelength of 210 nm. Preferably, a Beckman System Gold HPLC System may be used for chromatography of both proteins and digests. Using the chromatography protocol set forth as an example supra, Wohl-1 peptide may be expected to elute as peptide number 4 (see section 6, infra). Peptide fragments of PF4 may, according to the invention, be optionally chemically modified, and may be tested for angiogenic activity as set forth in the next section.

5.3. Identification of Angiogenic Peptides

Peptides as described supra may be determined to have angiogenic activity using any in vitro or in vivo assay system known in the art to evaluate a factor for angiogenic activity. The term angiogenic activity should be construed herein to refer to an ability to (i) induce the formation of new blood vessels and/or (ii) attract endothelial cells.

In a specific embodiment, peptides may be tested for angiogenic activity using an endothelial cell chemotaxis assay, for example, as described in section 6, infra. According to such a method endothelial cell movement in response to a particular peptide may be measured by detecting migration of endothelial cells into a porous membrane.

For example, endothelial cell migration may be assayed by a method such as that described in Banda et al. (1982, Proc. Natl. Acad. Sci. 79:7773–7777, incorporated by reference in its entirety herein). According to this method, solutions of peptides to be tested may be diluted about 1:10 in Dulbecco's modified Eagle's medium supplemented with 10 percent rabbit platelet-poor plasma serum and placed in the bottom of Boyden blind-well chambers. Then gelatin-coated 10-µm-pore-diameter polycarbonate filters (such as those available from Nucleopore) may be placed over the test solution and endothelial cells suspended in Dulbecco's modified Eagle's medium plus 10 percent platelet-poor serum may be added to the top compartment, and the chambers may be incubated for about 7 hours at 37° C. At the end of the incubation, the tops of the filters may be wiped clean, and the filters may be fixed, stained, and evaluated by counting the number of cells that migrated to the bottom side of the filter.

In another embodiment, peptides may be tested for angiogenic activity using an in vivo assay which tests for angiogenesis in vivo in response to a peptide of the invention comprised in an implant. According to a specific embodiment, rabbit corneal implant assay (RCIA) method may be used (Gimbrone et al., 1974, J. Natl. Cancer Instit. 52:413 which is incorporated by reference in its entirety herein). In the RCIA, the peptide to be tested is mixed with an inert vehicle such as hydron, a methacrylate polymer, and then dried. The resulting pellet is then implanted in the cornea of a rabbit 2–3 mm from the superior limbus. If the test peptide is angiogenic, capillary growth may be expected to initiate from the superior limbus and then grow toward the implant. A description of the RCIA method is provided in section 7, infra.

5.4. Utility of the Invention

The present invention provides for peptides and peptide derivatives related to PF4 which may be used to promote angiogenesis, and for methods of treating patients that would benefit from increased angiogenesis. The invention provides for methods of inducing angiogenesis in a tissue comprising exposing the tissue to an effective amount of a peptide or peptide derivative related to PF4 which exhibits angiogenic activity. Methods of treatment comprise the administration of an effective amount of a peptide of the invention to a patient in need of such treatment. Administration of the peptide may be systemic or localized. Methods of administration include, but are not limited to, intravenous, intramuscular, subcutaneous, intranasal, oral, or any other appropriate mode. The peptides of the invention may be administered in any suitable pharmacologic carrier. In certain circumstances, it may be desirable to administer the peptides of the invention comprised in an implant such that sustained release of the peptides may be achieved.

Patients who may benefit from increased angiogenesis include patients who suffer from vascular insufficiency, including arterial as well as venous insufficiency, systemically or in a localized area. Examples include patients who are suffering from diabetes or atherosclerosis or disorders of the microcirculation. Distinct areas which might benefit from treatment with angiogenic peptides include, but are not limited to, the extremities, the heart, and the cerebrovascular system. The angiogenic peptides of the invention may be particularly useful for promoting wound healing in diabetics.

The angiogenic peptides of the invention may also be used to promote wound healing in patients who may or may not suffer from vascular compromise. For example, wound healing may be generally promoted in surgical patients, trauma patients, burn patients, or in patients who have suffered damage to the cardiovascular system, including myocardial infarction. The peptides may also be useful in improving the cosmetic appearance resulting from wound healing, for example, in scar revision. The peptides of the invention may be useful in the treatment of acute as well as chronic wounds.

Such angiogenic peptides may also be useful in promoting the incorporation of a grafted piece of tissue by providing the tissue with improved blood perfusion. The present invention therefore also provides for methods for facilitating the assimilation of grafted tissue comprising exposing the grafted tissue to an effective concentration of angiogenic peptide.

The angiogenic peptides of the invention may be used for the treatment of human as well as animal subjects.

The present invention also contemplates the development of peptides structurally related to the angiogenic peptides of the invention which inhibit angiogenesis. Such anti-angiogenic peptides would be useful in the treatment of disorders of increased vascularization or in which it is desirable to limit the blood supply or vascularization, such as malignant tumors, hemangiomas, endothelial angiomatosis, rheumatoid arthritis and psoriasis.

6. EXAMPLE: PREPARATION OF ANGIOGENIC PEPTIDES

6.1. Materials and Methods

6.1.1. Preparation of PF4

PF4 was purified from thrombin-activated platelet extracts by a modification of the method described by Medici et al. (1989, Thrombos. Res. 54:277–287). PF4 was isolated by heparin sepharose affinity chromatography with elution of the factor at 1.7M NaCl, followed by strong cation exchange chromatography on a polysulfoethyl-aspartamide column eluted with NaCl in the presence of 15 percent acetonitrile and finally by separation on a Vydac RPC$_4$ reverse-phase HPLC analytical column eluted with a linear acetonitrile gradient in 0.1 percent TFA in water.

6.1.2. Tryptic Digestion of PF4

Tryptic digestion was performed by dissolving lyophilized PF4 in 50 μl of 0.4M Na$_2$CO$_3$/8M urea pH 9.0, in a microcentrifuge tube. The protein was then reduced by addition of 5 μl of 45 mM DTT in pH 9.0 buffer for 15 minutes at 50° C. The protein was carboxymethylated by addition of 5 μl of iodoacetic acid in 0.5N NaOH and incubated for 15 minutes in the dark, at room temperature. Finally, 140 μl deionized water and 5 μl of 1 mM HCl solution of sequencer grade trypsin (200 μg/ml) was added and the sample incubated for 24 hours at 37° C.

The tryptic digest was injected onto a Vydac C$_{18}$ column equilibrated with 2.7% Acetonitrile/0.1% TFA/H$_2$O and was chromatographed at a flow rate of 0.5 ml/min with 1.0 minute fractions collected. The elution pattern was as follows: 2.7% buffer B (95% acetonitrile) in buffer A (0.1% TFA in water) for 10 minutes, 2.7%–95% B in 123 minutes (see FIG. 1). The elution of the peptides was monitored at 210 nm. A Beckman System Gold HPLC System was used for chromatography of both proteins and digests.

6.1.3. Endothelial Cell Chemotaxis Assay

6.1.3.1. Preparation of Cells

Rabbit wound capillary endothelial cells (RWCE) were grown to 60–85 percent confluency on 3–4 Primaria (Falcon #3824) 75 cm$^2$ flasks. Approximately 20–24 hours before the assay, the media was removed and the flasks were rinsed twice with Ca/Mg-free Hank's Balanced Salt Solution. Then 12–15 ml of 0.1% lactalbumin in MEDIA 199 (Media-Tech) was added to each flask and the cultures were maintained overnight. The next day, the lactalbumin/media was removed from the flasks and the cells were rinsed with 6–10 ml HBSS. The endothelial cells were then removed from the flasks by incubating the cells for 14 minutes at room temperature in an enzyme cocktail consisting of 2×10$^5$ KU DNAase (approximately 100 mg) and 1×10$^5$ U collagenase (approximately 335 mg) per liter of HBSS (Ca/Mg free). The cells were then scraped from the bottom of the flask and then washed by centrifugation in 0.2 percent lactalbumin/M199 medium. The number of viable cells were determined prior to the migration assay by trypan blue exclusion.

6.1.3.2. Preparation of Filters

Nucleopore polypropylene filters (8.0 µm pores, PVPF, from Neuro Probe, Inc.) were used in the experiment. One side of the filter was coated with a fibronectin solution (1 µg fibronectin per ml HBSS; 3–4 ml were used to coat each filter by putting the solution in a petri dish and then laying the filter over the fibronectin solution).

6.1.3.3. Preparation of Chambers

A Neuro Probe 48 well chemotaxis chamber was used for the experiment. Test peptides, in volumes of about 26 µl, were added to the wells of the lower chamber. The filter, coated with fibronectin and prepared as above, was then laid over the bottom wells. The top chamber was then attached, and the endothelial cell suspension (0.75–10$^6$ cells per ml) was added to most of the wells of the top chamber; the remaining wells were filled with cell-free medium as a control. The chamber was then incubated for 4 hours at 37° C. in a 5% $CO_2$, humid atmosphere.

6.1.3.4. Removal and Wiping of Filter

The filter was removed from the apparatus. If the bottom chamber contained an angiogenic peptide, the cells from the top layer would have migrated into and through the filter. However, non-migrated cells which simply adhered to the filter needed to be removed. Therefore, the portion of the filter which had been in contact with the cell-containing chamber was wet in phosphate buffered saline (PBS) and the cells were cleared from this surface using a wiper blade. The filter, which at that point substantially contained migrated cells, was then dried overnight, stained in Leukostat (Fisher), and the absorbance of portions of the filter were read using a densitomer. Relative increases in the densitometry tracing were indicative of greater cell migration and therefore of angiogenic activity of the test peptide contained in the corresponding lower chamber.

6.2. Results and Discussion

Peptide 4 was sequenced in a Porton 2090e sequencer after adsorption onto a Porton proprietary peptide support. The sequence of the peptide was: Thr-27.5 pm, Thr-23.5 pm, Ser-30.0 pm, Gln-26.5 pm, Val-22.6 pm, Arg-10.5 pm, Pro-9.2 pm, Arg-4.7 pm. Amino acid analysis using the Beckman Dabsyl Chloride method confirmed the total sequence of the peptide. More consistent results were observed using the rabbit corneal implant assay system modeled after the work of Gimbrone et al. (1974, J. Natl. Cancer Inst. 52:413–427) and Langer et al. (1976, Nature 263:797–800 (see section 7, infra)) than with the capillary endothelial cell chemotaxis assay. Our results yielded +2 and ∓ angiogenic responses (on a scale of 1 to 4) in at least six different experiments in addition to the data summarized in FIG. 3. FIG. 3 summarized results with the original octapeptide (peptide 1), and with seven peptide analogs that were synthesized by the Merrifield method (Barany and Merrifield (1980), in "The Peptides" Vol. 2, Gross and Meienhofer, eds., Academic Press, N.Y.). The results in FIG. 3 show clearly that as compared to control implant, all of the peptides induced some angiogenic response, but octapeptide 1 and pentapeptide 6 induced very strong and specific angiogenic responses which were also inflammation-free.

7. EXAMPLE: ANGIOGENIC EFFECTS OF PEPTIDES IN RABBIT CORNEAL IMPLANT STUDY

7.1. Materials and Methods

7.1.1. Preparation of Implant

Implant pellets were prepared by mixing a solution of 10 percent hydron, 1 percent polyethylene glycol, and 70 percent ethanol with an equal volume of test peptide (50 µl hydron solution: 50 µl peptide solution containing about 5–10 µg of peptide). The resulting mixture was vigorously vortexed, and 20 µl aliquots were then placed on a sheet of plastic and desiccated to form dry pellets. Each pellet contained about 1 or 2 µg of test peptide.

7.1.2. Surgical Procedure

The resulting implants were placed in the corneas of rabbits under general anesthesia approximately 2–3 mm from the superior limbus capillary bed. The pellets did not lie closer than 1 mm from the capillary bed.

7.1.3. Monitoring Angiogenesis

The eyes were checked on days 3, 5, and 7 for direct growth of capillaries towards the pellet, and were graded according to FIG. 4 (Gimbrone et al. 1974, J. Natl. Cancer Inst. 52:413–427). Photographs were taken of the eyes on day 5 and/or 7 to record capillary growth. On day 7, the animals were sacrificed and the corneas were examined histologically (with hematoxylin and eosin stain) for capillary growth.

7.2. Results and Discussion

Visual examination of angiogenesis was scored on day 7 from 0 to +4 depending on the extent of capillary migration. The angiogenic index (AI) was calculated by the formula $$AI = (\text{total score}/n \times 8) \times 100,$$

the score being determined by assigning the following numerical values to observed angiogenesis:

| | |
|---|---|
| negative = | 0 |
| +/− = | 1 |
| +1 = | 2 |
| +2 = | 4 |
| +3 = | 6 |
| +4 = | 8 |

The angiogenic activity of peptides Wohl 1–8 is shown in Table I. Each of the eight peptides was observed to be superior to control implants in the rabbit corneal implant assay (RCIA), with peptides Wohl-1 and Wohl-6 appearing particularly active.

The results of histological evaluation of the angiogenic activity of 1.0 µg/implant as compared to 2.0 µg/implant is shown in Table II. The 1.0 µg/implant was found to exhibit a higher angiogenic index than the 2.0 µg/implant.

TABLE I

| Visual Angiogenic Activity of Peptides | | |
|---|---|---|
| Peptide | Number of Observations | Angiogenic Index |
| Wohl-1 | 24 | 45 |
| Wohl-2 | 8 | 34 |
| Wohl-3 | 7 | 32 |
| Wohl-4 | 8 | 23 |
| Wohl-5 | 8 | 36 |
| Wohl-6 | 8 | 42 |
| Wohl-7 | 8 | 31 |
| Wohl-8 | 7 | 30 |
| Control Implants | 24 | 17 |

TABLE II

Histological Angiogenic Activity of C8-1

| Peptide | Number of Observations | Angiogenic Index |
| --- | --- | --- |
| 1.0 μg/implant | 11 | 84 |
| 2.0 μg/implant | 7 | 59 |
| Control Implants | 16 | 31 |

The present invention has been described in detail with particular reference to the above embodiments. It will be understood, however, that the present invention is not to be limited in scope by the embodiments disclosed which are intended as illustrations of aspects of the invention.

Indeed, various modifications of the invention in addition to those shown and described herein will become apparent to those skilled in the art from the foregoing description. Such modifications are intended to fall within the scope of the appended claims.

Various references have been cited herein; these are incorporated by reference, in their entirety.

What is claimed is:

1. An angiogenic peptide consisting of the amino acid sequence Thr-Thr-Ser-Gln-Val-Arg-Pro-Arg.

2. A pharmaceutical composition comprising the peptide of claim 1 in a pharmacologically suitable carrier.

3. An angiogenic peptide consisting of the amino acid sequence Val-Lys-Thr-Thr-Ser-Gln-Val-Arg-Pro-Arg.

4. A pharmaceutical composition comprising the peptide of claim 3 in a pharmacologically suitable carrier.

5. An angiogenic peptide consisting of the amino acid sequence Ser-Gln-Val-Arg-Pro-Arg.

6. A pharmaceutical composition comprising the peptide of claim 5 in a pharmacologically suitable carrier.

7. An angiogenic peptide consisting of the amino acid sequence Val-Arg-Pro-Arg.

8. A pharmaceutical composition comprising the peptide of claim 7 in a pharmacologically suitable carrier.

9. An angiogenic peptide consisting of the amino acid sequence Thr-Thr-Ser-Gln-Val-Arg-Pro-Arg-His-Ile-Thr.

10. A pharmaceutical composition comprising the peptide of claim 9 in a pharmacologically suitable carrier.

11. An angiogenic peptide consisting of the amino acid sequence Thr-Thr-Ser-Gln-Val.

12. A pharmaceutical composition comprising the peptide of claim 11 in a pharmacologically suitable carrier.

13. An angiogenic peptide consisting of the amino acid sequence Thr-Ser-Gln-Val-Arg.

14. A pharmaceutical composition comprising the peptide of claim 13 in a pharmacologically suitable carrier.

15. An angiogenic peptide consisting of the amino acid sequence Thr-Thr-Ser-Gly-Ile-His-Pro-Lys.

16. A pharmaceutical composition comprising the peptide of claim 15 in a pharmacologically suitable carrier.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
    ( A ) LENGTH: 101 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:1:

```
Met   Ser   Ser   Ala   Ala   Gly   Phe   Cys   Ala   Ser   Arg   Pro   Gly   Leu   Leu   Phe
 1                       5                             10                            15

Leu   Gly   Leu   Leu   Leu   Leu   Pro   Leu   Val   Val   Ala   Phe   Ala   Ser   Ala   Glu
                   20                            25                            30

Ala   Glu   Glu   Asp   Gly   Asp   Leu   Gln   Cys   Leu   Cys   Val   Lys   Thr   Thr   Ser
             35                            40                      45

Gln   Val   Arg   Pro   Arg   His   Ile   Thr   Ser   Leu   Glu   Val   Ile   Lys   Ala   Gly
       50                       55                            60

Pro   His   Cys   Pro   Thr   Ala   Gln   Leu   Ile   Ala   Thr   Leu   Lys   Asn   Gly   Arg
 65                             70                      75                            80

Lys   Ile   Cys   Leu   Asp   Leu   Gln   Ala   Pro   Leu   Tyr   Lys   Lys   Ile   Ile   Lys
                         85                            90                            95

Lys   Leu   Leu   Glu   Ser
                    100
```

( 2 ) INFORMATION FOR SEQ ID NO:2:

( i ) SEQUENCE CHARACTERISTICS:
    ( A ) LENGTH: 8 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:2:

```
Thr   Thr   Ser   Gln   Val   Arg   Pro   Arg
 1                       5
```

( 2 ) INFORMATION FOR SEQ ID NO:3:

( i ) SEQUENCE CHARACTERISTICS:
    ( A ) LENGTH: 10 amino acids
    ( B ) TYPE: amino acid
    ( C ) STRANDEDNESS: unknown -continued ( D ) TOPOLOGY: unknown ( i i ) MOLECULE TYPE: peptide ( x i ) SEQUENCE DESCRIPTION: SEQ ID NO:3:

```
Val  Lys  Thr  Thr  Ser  Gln  Val  Arg  Pro  Arg
1                   5                        10
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

```
Ser  Gln  Val  Arg  Pro  Arg
1                   5
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

```
Val  Arg  Pro  Arg
1
```

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

```
Thr  Thr  Ser  Gln  Val  Arg  Pro  Arg  His  Ile  Thr
1                   5                        10
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

```
Thr  Thr  Ser  Gln  Val
1                   5
```

( 2 ) INFORMATION FOR SEQ ID NO:8:

( i ) SEQUENCE CHARACTERISTICS:
        ( A ) LENGTH: 5 amino acids
        ( B ) TYPE: amino acid

```
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:8:

Thr  Ser  Gln  Val  Arg
   1                    5

( 2 ) INFORMATION FOR SEQ ID NO:9:

( i ) SEQUENCE CHARACTERISTICS:
            ( A ) LENGTH: 8 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:9:

Thr  Thr  Ser  Gly  Ile  His  Pro  Lys
   1                    5

( 2 ) INFORMATION FOR SEQ ID NO:10:

( i ) SEQUENCE CHARACTERISTICS:
            ( A ) LENGTH: 3 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:10:

Thr  Ser  Gln
   1

( 2 ) INFORMATION FOR SEQ ID NO:11:

( i ) SEQUENCE CHARACTERISTICS:
            ( A ) LENGTH: 3 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:11:

Val  Arg  Pro
   1

( 2 ) INFORMATION FOR SEQ ID NO:12:

( i ) SEQUENCE CHARACTERISTICS:
            ( A ) LENGTH: 4 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:12:

Thr  Thr  Ser  Gln
   1
```